(12) United States Patent
Charles et al.

(10) Patent No.: US 6,455,510 B1
(45) Date of Patent: Sep. 24, 2002

(54) CHEMICAL COMPOUNDS

(75) Inventors: Richard Peter Charles, Stevenage (GB); Brian Cox, Stevenage (GB); Colin David Eldred, Stevenage (GB); Andrew Michael Kenneth Pennell, San Francisco, CA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/530,573

(22) PCT Filed: Nov. 6, 1998

(86) PCT No.: PCT/EP98/07021

§ 371 (c)(1),
(2), (4) Date: Jun. 15, 2000

(87) PCT Pub. No.: WO99/24449

PCT Pub. Date: May 20, 1999

(30) Foreign Application Priority Data

Nov. 8, 1997 (GB) .............................................. 9723589

(51) Int. Cl.$^7$ .......................... A61K 31/70; C07H 19/16
(52) U.S. Cl. ........................................ 514/46; 536/27.3
(58) Field of Search ............................ 514/46; 536/27.3

(56) References Cited

U.S. PATENT DOCUMENTS 3,575,959 A  4/1971  Shen

FOREIGN PATENT DOCUMENTS

| WO | WO 95 07921 A | 3/1995 |
| WO | WO 97 33591 A | 9/1997 |
| WO | WO 97 43300 A | 11/1997 |
| WO | WO99/24449 A2 * | 5/1999 |

OTHER PUBLICATIONS

Moos W.H. et al., "N6–Cycloalkyladenosines Potent A1–Selective Adenosine Agonists" Journal of Medicinal Chemistry, Oct. 1, 1985, XP002038896.

Lubitz Von D.K.J.E. et al., "Reduction of Postichemic Brain Damage and Memory Dificits Following Treatment with the Selective Adenosine A1 Receptor Agonist" European Journal of Pharmacology, Jan. 1, 1996, XP002035719.

Poulsen et al., "Adenosine Receptors: New Opportunities for Future Drugs," *Bioorganic & Medicinal Chemistry*, 6, 619–641 (1998).*

* cited by examiner

*Primary Examiner*—Paul J. Killos
*Assistant Examiner*—Lawerence E Crane
(74) *Attorney, Agent, or Firm*—Bacon & Thomas

(57) ABSTRACT

A compound of formula (I) which is an agonist at the adenosine A1 receptor wherein $R^2$ represents $C_{1-3}$alkyl, halogen or hydrogen; $R^3$ represents a fluorinated straight or branched alkyl group of 1–6 carbon atoms and salts and solvates thereof, in particular, physiologically acceptable solvates and salts thereof. These compounds are agonists at the adenosine A1 receptor.

21 Claims, No Drawings

CHEMICAL COMPOUNDS

This is a national stage application filed under 35 U.S.C. §371 of PCT International Application No. PCT/EP98/07021, filed Nov. 6, 1998; which claims priority from UK 9723589.9, filed Nov. 8, 1997.

The present invention relates to novel adenosine derivatives, to processes for their preparation, to pharmaceutical compositions containing them and to their use in medicine.

Thus the invention provides compounds of formula (I) which are agonists at the adenosine A1 receptor

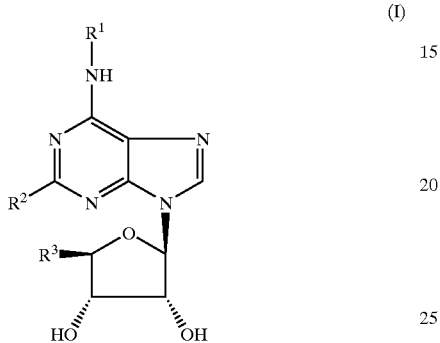

(I)

wherein
$R^2$ represents $C_{1-3}$alkyl, halogen or hydrogen;
$R^3$ represents a fluorinated straight or branched alkyl group of 1–6 carbon atoms;
$R^1$ represents a group selected from
(1) -(alk)$_n$-($C_{3-7}$)cycloalkyl, including bridged cycloalkyl, said cycloalkyl group being optionally substituted by one or more substituents selected from OH, halogen, —($C_{1-3}$) alkoxy, wherein (alk) represents $C_{1-3}$alkylene and n represents 0 or 1.
(2) an aliphatic heterocyclic group of 4 to 6 membered rings containing at least one heteroatom selected from O, N or S, optionally substituted by one or more substituents selected from the group consisting of —($C_{1-3}$)alkyl, —$CO_2$—($C_{1-4}$)alkyl, —CO($C_{1-3}$alkyl), —S(=O)$_n$—($C_{1-3}$alkyl), —CONR$^a$R$^b$ (wherein R$^a$ and R$^b$ independently represent H or $C_{1-3}$alkyl) or =O; where there is a sulfur atom in the heterocyclic ring, said sulfur is optionally substituted by (=O)$_n$, where n is 1 or 2.
(3) Straight or branched $C_{1-12}$ alkyl, optionally including one or more O, S(=O)$_n$ (where n is 0, 1 or 2) or N groups substituted within the alkyl chain, said alkyl optionally substituted by one or more of the following groups, phenyl, halogen, hydroxy or NR$^a$R$^b$ wherein R$^a$ and R$^b$ both represent $C_{1-3}$alkyl or hydrogen.
(4) a fused bicyclic aromatic ring

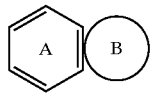

wherein B represents a 5 or 6 membered heterocyclic aromatic group containing 1 or more O, N or S atoms, wherein the bicyclic ring is attached to the nitrogen atom of formula (I) via a ring atom of ring A and ring B is optionally substituted by —$CO_2$—($C_{1-3}$alkyl).

(5) a phenyl group optionally substituted by one or more substituents selected from:
-halogen, —$SO_3H$, -(alk)$_n$OH, -(alk)$_n$-cyano, —(O)$_n$—($C_{1-6}$)alkyl (optionally substituted by one or more halogens), -(alk)$_n$-nitro, —(O)$_m$-(alk)$_n$-$CO_2R^c$, -(alk)$_n$)- CONR$^c$R$^d$-(alk)$_n$—COR$^c$, -(alk)$_n$—SOR$^e$, -(alk)$_n$-$SO_2R^e$, -(alk)$_n$-$SO_2NR^cR^d$,
(alk)$_n$OR$^c$, -(alk)$_n$-(CO)$_m$—$NHSO_2R^e$, -(alk)$_n$-NHCOR$^c$, -(alk)$_n$-NR$^c$R$^d$ wherein m and n are 0 or 1 and alk represents a $C_{1-6}$alkylene group or $C_{2-6}$ alkenyl group.
(6) A phenyl group substituted by a 5 or 6 membered heterocyclic aromatic group, said heterocyclic aromatic group optionally being substituted by $C_{1-3}$alkyl or NR$^c$R$^d$.
R$^c$ and R$^d$ may each independently represent hydrogen, or $C_{1-3}$ alkyl or when part of a group NR$^c$R$^d$, R$^c$ and R$^d$ together with the nitrogen atom may form a 5 or 6 membered heterocyclic ring optionally containing other heteroatoms, which heterocyclic ring may optionally be substituted further by one or more $C_{1-3}$ alkyl groups.
R$^e$ represents $C_{1-3}$alkyl
and salts and solvates thereof, in particular, physiologically acceptable solvates and salts thereof.

Conveniently the adenosine A1 agonists of the general formula (I) above exhibit greater activity at the adenosine A1 receptor than the other adenosine receptor subtypes, particularly A3. More particularly the compounds exhibit little or no activity at the the A3 receptor.

It will be appreciated that wherein $R^1$ and/or $R^2$ in compounds of formula (I) contain one or more asymmetric carbon atoms the invention includes all diastereoisomers of compounds of formula (I) and mixtures thereof. Otherwise the stereochemical configuration of compounds of the invention is as depicted in formula (I) above.

As used herein, the term "alkyl" means a straight or branched chain alkyl group. Examples of suitable alkyl groups within $R^1$ and $R^2$ include methyl, ethyl, n-propyl, i-propyl, n-butyl, s-butyl, t-butyl and 2,2-dimethylpropyl.

As used herein, the term "alkylene" means a straight or branched chain alkylene group containing 1–6 carbon atoms, e.g. methylene.

As used herein, the term "$C_{2-6}$alkenyl" means a straight or branched chain alkenyl group containing 2 to 6 carbon atoms. Allyl represents an example of a suitable $C_{2-6}$alkenyl group.

The term "halogen" means fluorine, chlorine, bromine or iodine.

By aliphatic heterocyclic group is meant a cyclic group of 4–6 carbon atoms wherein one or more of the carbon atoms is/are replaced by heteroatoms independently selected from nitrogen, oxygen or sulfur. This group may optionally be substituted as defined hereinabove.

The term heterocyclic aromatic group refers to an aromatic mono or bicyclic ring system comprising from 5 to 10 carbon atoms wherein one or more of the carbon atoms is/are replaced by heteroatoms independently selected from nitrogen, oxygen and sulfur, which ring system may optionally be substituted as defined hereinabove.

Pharmaceutically acceptable salts of the compounds of formula (I) include those derived from pharmaceutically acceptable inorganic and organic acids. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids. A particularly suitable pharmaceutically acceptable salt of the compounds of formula (I) is the hydrochloride salt. Other acids such as oxalic, while not, in themselves pharmaceutically acceptable, may be useful as intermediates in obtaining the compounds of the invention and their pharmaceutically acceptable acid addition salts. The solvates may be, for example, hydrates.

$R^3$ preferably represents a $C_{1-3}$ fluoroalkyl group especially a fluoromethyl or fluoroethyl group more preferably $F_2C(Me)$—, $FCH_2$—.

$R^2$ preferably represents hydrogen, methyl or halogen, more preferably hydrogen or chlorine.

Conveniently, $R^1$ may represent $(alk)_n$-$C_{3-6}$ cycloalkyl wherein n is 0 or 1 and the said cycloalkyl is either substituted by at least one substituent selected from halogen, particularly fluorine, and OH or is unsubstituted. Preferably n is zero. More preferably, the cycloalkyl group is monosubstituted with either OH or fluorine and more preferably the cycloalkyl ring has 5 carbon members.

Alternatively $R^1$ may represent a substituted or unsubstituted aliphatic heterocyclic group, the substituent being selected from the group consisting of —$CO_2$—$(C_{1-4})$alkyl, —CO—$(C_{1-3})$alkyl, —$S(=O)_n$—$(C_{1-3})$alkyl, $CONR^aR^b$ (wherein $R^a$ and $R^b$ are defined herein above), and when there is a heteroatom S in the ring this heteroatom may optionally be substituted by $(=O)_n$ where n is 1 or 2. More preferably the heterocyclic ring is unsubstituted or substituents are —$CO_2$—$(C_{1-4})$alkyl, or when the heteroatom is S, the substituent $(=O)_n$ is attached to the heterocyclic sulfur atom.

Conveniently, the aliphatic heterocyclic group is unsubstituted or when the substituent is —$CO_2(C_{1-4})$alkyl, the heteroatom is N and the substituent is directly attached to said ring nitrogen atom.

Preferably the heterocyclic ring is 6 membered and more preferably contains only one O, N or S heteroatom.

Alternatively, $R^1$ may represent a straight or branched alkyl of 1–6 carbon atoms optionally with at least one $S(=O)_n$ and/or N substituted in the chain, where there is an $S(=O)_n$ in the chain, preferably n is 1 or 2. The alkyl group conveniently may be unsubstituted or substituted by at least one OH group.

Alternatively $R^1$ may represent a phenyl group which is substituted by one or more substituents selected from OH and halogen. Preferably the phenyl is disubstituted in the 2,4 positions. Preferably both substituents are halogen more particularly, fluorine and chlorine. For example, a particularly preferred combination is 2-fluoro and 4-chloro.

It is to be understood that the present invention covers all combinations of particular and preferred groups mentioned above.

Particular compounds according to the invention include:

5'-deoxy-5'-fluoro-N-(tetrahydro-pyran-4-yl)-adenosine,
5'-deoxy-5'-fluoro-2-methyl-N-(tetrahydro-pyran-4-yl)-adenosine,
2-chloro-5'-deoxy-5'-fluoro-N-(tetrahydro-pyran-4-yl)-adenosine,
(2R,3R,4S,5S)-2-[2-Chloro-6-(tetrahydro-pyran-4-ylamino)-purin-9-yl]-5-trifluoromethyl-tetrahydro-furan-3,4-diol,
2-chloro-5'-deoxy-5'-fluoro-N-(2R-fluoro-cyclopent-(R)-yl)-adenosine,
2-chloro-5'-deoxy-5'-fluoro-N-(2S-hydroxy-cyclopent-(S)-yl)-adenosine,
N-(endo-bicyclo[2.2.1]hept-2-yl)-2-chloro-5'-deoxy-5'-fluoro-adenosine,
4-[2-chloro-9-(5S-fluoromethyl-3R,4S-dihydroxy-tetrahydro-furan-2R-yl)-9H-purin-6-ylamino]-piperidine-1-carboxylic acid ethyl ester,
1-{4-[2-chloro-9-(5S-fluoromethyl-3R,4S-dihydroxy-tetrahydro-furan-2R-yl)-9H-purin-6-ylamino]-piperidin-1-yl}-ethanone,
N-(endo-bicyclo[2.2.1]hept-2-yl)-5'-deoxy-5'-fluoro-adenosine,
N-(exo-bicyclo[2.2.1]hept-2-yl)-5'-deoxy-5'-fluoro-adenosine,
5'-deoxy-5'-fluoro-N-(2S-hydroxy-cyclopent-(S)-yl)-adenosine,
4-[9-(5S-fluoromethyl-3R,4S-dihydroxy-tetrahydro-furan-2R-yl)-9H-purin-6-ylamino)-piperidine-1-carboxylic acid ethyl ester,
2-chloro-5'-deoxy-N-(1,1-dioxo-hexahydro-1.delta.6-thiopyran-4-yl)-5'-fluoro-adenosine,
2-chloro-5'-deoxy-N-(2,3-dihydroxy-propyl)-5'-fluoro-adenosine,
(2R,3R,4S,5S)-2-[6-(cyclopropylmethyl-amino)-purin-9-yl]-(1,1-difluoroethyl)-tetrahydro-furan-3,4-diol,
(2R,3R,4S,5S)-2-[6-(bicyclo[2.2.1]hept-2-ylamino)-purin-9-yl]-5-(1,1-difluoro-ethyl)-tetrahydro-furan-3,4-diol,
2-[9-(5S-fluoromethyl-3R,4R-dihydroxy-tetrahydro-furan-2R-yl)-9H-purin-6-ylamino]-ethanesulfonic acid methylamide,
5'-deoxy-5'-fluoro-N-(2,2-dimethyl-propyl)-adenosine,
N-tert-butyl-5'-deoxy-5'-fluoro-adenosine,
5'-deoxy-5'-fluoro-N-(tetrahydro-thiopyran-4-yl)-adenosine,
2-chloro-5'-deoxy-5'-fluoro-N-isobutyl-adenosine,
2-chloro-5'-deoxy-5'-fluoro-N-(1-methanesulfonylpiperidin-4-yl)-adenosine,
2-Chloro-5'-deoxy-N-(2,2-dimethyl-propyl)-5'-fluoro-adenosine,
N-(exo-Bicyclo[2.2.1]hept-2-yl)-2-chloro-5'-deoxy-5'-fluoro-adenosine,
4-[2-chloro-9-(5S-fluoromethyl-3R,4S-dihydroxy-tetrahydro-furan-2R-yl)-9H-6-ylamino]-piperidine-1-carboxylic acid butyl ester,
5'-deoxy-N-(1,1-dioxo-hexahydro-1.delta.6-thiopyran-4-yl)-5'-fluoroadenosine purin-6-ylamino]-piperidine-1-carboxylic acid ethylamide,
N-(4-chloro-2-fluoro-phenyl)-5'-deoxy-5'-fluoroadenosine,
4-[2-chloro-9-(5S-fluoromethyl-3R,4S-dihydroxy-tetrahydro-furan-2R-yl)-9H-purin-6-ylamino]piperidine-1-carboxylic acid ethylamide.

Compounds according to the invention have applicability as inhibitors of lipolysis i.e. they decrease plasma free fatty acid concentrations. The compounds may thus be used in the treatment of hyperlipidaemias. Furthermore, as a consequence of their anti-lipolytic activity, the compounds have the ability to lower elevated blood glucose, insulin and ketone body levels and therefore may be of value in the therapy of diabetes. Since anti-lipolytic agents have hypolipidaemic and hypofibrinogenaemic activity, the compounds may also show anti-atherosclerotic activity. The anti-lipolytic activity of compounds of the invention has been demonstrated by their ability to lower the concentration of non-esterified fatty acids (NEFA) in starved rats dosed orally according to the method described by P. Strong et al. in Clinical Science (1993), 84, 663–669.

In addition to their anti-lipolytic effect, the compounds of the invention may independently affect cardiac function by reducing heart rate and conduction. The compounds may thus be used in the therapy of a number of cardiovascular disorders, for example cardiac arrythmias, particularly following myocardial infarction, and angina.

Furthermore, the compounds of the invention are useful as cardioprotective agents, having applicability in the treatment of ischaemic heart disease. As used herein the term "ischaemic heart disease" includes damage associated with both myocardial ischaemia and reperfusion, for example, associated with coronary artery bypass grafting (CABG), percutaneous translumenal coronary angioplasty (PTCA), cardioplegia, acute myocardial infarction, thrombolysis, stable and unstable angina and cardiac surgery including in particular cardiac transplantation. The compounds of the invention additionally are useful for treating ischaemic damage to other organs. The compounds of the invention may also be valuable in the treatment of other disorders arising as a result of widespread atheromatous disease, for example, peripheral vascular disease (PVD) and stroke.

The compounds may also inhibit renin release and thus be of use in the therapy of hypertension and heart failure. The compounds may also be useful as CNS agents (e.g. as hypnotics, sedatives, analgesics and/or anti-convulsants particularly finding use in the treatment of epilepsy).

In addition, the compounds of the invention may find use in the treatment of sleep apnoea.

The compound of formula (I) and pharmaceutically acceptable acid addition salts thereof are useful as analgesics. They are therefore useful in treating or preventing pain. They may be used to improve the condition of a host, typically of a human being, suffering from pain. They may be employed to alleviate pain in a host. Thus, the compound of formula (I) and its pharmaceutically acceptable acid addition salts may be used as a preemptive analgesic to treat acute pain such as musculoskeletal pain, post operative pain and surgical pain, chronic pain such as chronic inflammatory pain (e.g. rheumatoid arthritis and osteoarthritis), neuropathic pain (e.g. post herpetic neuralgia,. trigeminal neuralgia, neuropathies associated with diabetes and sympathetically maintained pain) and pain associated with cancer and fibromyalgia. The compound of formula (I) may also be used in the treatment or prevention of pain associated with migraine, tension headache and cluster headaches and pain associated with Functional Bowel Disorders (e.g. IBS), non cardiac chest pain and non ulcer dyspepsia.

Accordingly, the invention provides a compound of formula (I) or a physiologically acceptable salt or solvate thereof for use in therapy, and in particular in the treatment of human or animal subjects suffering from a condition in which there is an advantage in decreasing plasma free fatty acid concentration, or reducing heart rate and conduction, or whereby the therapy involves the treatment of ischaemic heart disease, peripheral vascular disease or stroke or which subject is suffering from a CNS disorder, sleep apnoea or pain.

In a further aspect, the invention provides a method of treatment of a human or animal subject suffering from a condition in which there is an advantage in decreasing plasma free fatty acid concentration, or reducing heart rate and conduction, or which subject is suffering from or susceptible to ischaemic heart disease, peripheral vascular disease or stroke, or which subject is suffering a CNS disorder or suffering from sleep apnoea or suffering pain, which method comprises administering to the subject an effective amount of a compound of formula (I) or a pharmaceutically acceptable salt or solvate thereof.

In a further aspect, the invention provides the use of a compound of formula (I) or a pharmaceutically acceptable salt or solvate thereof for the manufacture of a medicament for the treatment of a human or animal suffering from a condition in which there is an advantage in decreasing plasma free fatty acid concentration, or reducing heart rate and conduction, or which subject is suffering from or susceptible to ishaemic heart disease, peripheral vascular disease or stroke, or which subject is suffering a CNS disorder or suffering from sleep apnoea or suffering pain.

In respect of the above mentioned ischaemic treatment, it has been found that according to a particularly unexpected aspect of the present invention, not only does administration of a compound of formula (I) prior to ischaemia provide protection against myocardial infarction, but protection is also afforded if the compound of formula (I) is administered after the ischaemic event and before reperfusion. This means that the methods of the present invention are applicable not only where ischaemia is planned or expected, for example in cardiac surgery, but also in cases of sudden or unexpected ischaemia, for example in heart attack and unstable angina.

It will be appreciated that reference to treatment includes acute treatment or prophylaxis as well as the alleviation of established symptoms.

In yet a further aspect, the invention provides a pharmaceutical composition comprising at least one compound of formula (I) or a pharmaceutically acceptable salt or solvate thereof in association with a pharmaceutical carrier and/or excipient.

In another aspect, the invention provides a pharmaceutical composition comprising, as active ingredient, at least one compound of formula (I) or a pharmaceutically acceptable salt or solvate thereof in association with a pharmaceutical carrier and/or excipient for use in therapy, and in particular in the treatment of human or animal subjects suffering from a condition in which there is an advantage in decreasing plasma free fatty acid concentration, or reducing heart rate and conduction, or which subject is suffering from or susceptible to ischaemic heart disease, peripheral vascular disease or stroke, or which subject is suffering from a CNS disorder, sleep apnoea or pain.

There is further provided by the present invention a process of preparing a pharmaceutical composition, which process comprises mixing at least one compound of formula (I) or a pharmaceutically acceptable salt or solvate thereof, together with a pharmaceutically acceptable carrier and/or excipient.

Compositions according to the invention may be formulated for topical, oral, buccal, parenteral or rectal administration or in a form suitable for administration by inhalation or insufflation. Oral administration is preferred. The compositions may be adapted for sustained release.

For topical administration, the pharmaceutical composition may conveniently be given in the form of a transdermal patch.

Tablets and capsules for oral administration may contain conventional excipients such as binding agents, for example mucilage of starch or polyvinylpyrrolidone; fillers, for example, lactose, microcrystalline cellulose or maize-starch;

lubricants, for example, magnesium stearate or stearic acid; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, or carboxymethyl cellulose: emulsifying agents, for example, sorbitan mono-oleate; non-aqueous vehicles (which may include edible oils), for example, propylene glycol or ethyl alcohol; and preservatives, for example, methyl or propyl p-hydroxybenzoates or sorbic acid. The preparations may also contain buffer salts, flavouring, colouring and sweetening agents (e.g. mannitol) as appropriate.

For buccal administration the compositions may take the form of tablets or lozenges formulated in conventional manner.

The compounds of formula (I) may be formulated for parenteral administration by bolus injection or continuous infusion and may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of formula (I) may also be formulated as suppositories, e.g. containing conventional suppository bases such as cocoa butter or other glycerides.

A proposed dose of the compounds of the invention for administration to man (of approximately 70 kg body weight) is 1 mg to 2 g, preferably 1 mg to 100 mg, of the active ingredient per unit dose which could be administered, for example, 1 to 4 times per day. It will be appreciated that it may be necessary to make routine variations to the dosage, depending on the age and condition of the patient. The dosage will also depend on the route of administration.

In a yet further aspect the invention also provides for the use of a compound of formula (I) or a pharmaceutically acceptable salt or solvate thereof for the manufacture of a medicament for the treatment of human or animal subjects suffering from a condition in which there is an advantage in decreasing plasma free fatty acid concentration, or reducing heart rate and conduction, or which subject is suffering from or susceptible to ischaemic heart disease, peripheral vascular disease (PVD) or stroke, or which patient is suffering from a CNS disorder, sleep apnoea or pain.

The compounds of formula (I) and physiologically acceptable salts or solvates thereof may be prepared by the processes described hereinafter, said processes constituting a further aspect of the invention. In the following description, the groups $R^1$, $R^2$ and $R^3$ are as defined for compounds of formula (I) unless otherwise stated.

According to a first general process (A), a compound of formula (I) may be prepared by reacting a compound of formula (II).

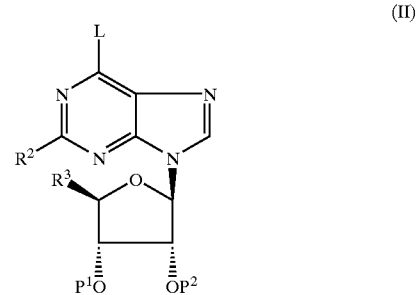

wherein, L represents a leaving group such as a halogen atom (e.g. a chlorine atom) and $P^1$ and $P^2$ represent hydrogen or a suitable protecting group (e.g. acetyl) with a compound of formula $R^1NH_2$ or a salt thereof, under basic conditions.

Compounds of formula (II) may be used to produce compounds of formula (I) directly by reaction with the group $R^1NH_2$ either in the absence or presence of a solvent such as an alcohol (e.g. a lower alkanol such as isopropanol, t-butanol or 3-pentanol), an ether (e.g. tetrahydrofuran or dioxan), a substituted amide (e.g. dimethylformamide), a halogenated hydrocarbon (e.g. chloroform) or acetonitrile, preferably at an elevated temperature (e.g. up to the reflux temperature of the solvent), in the presence of a suitable acid scavenger, for example, inorganic bases such as sodium or potassium carbonate, or organic bases such as triethylamine, diisopropylethylamine or pyridine.

This reaction may be preceded or followed where appropriate by in situ removal of the $P^1$ and $P^2$ protecting groups. For example when $P^1$ and $P^2$ represent acetyl, this may be effected with an amine such as ammonia or tert-butylamine in a solvent such as methanol at a convenient temperature.

Compounds of formula (II) may be prepared by the reaction of a compound of formula (III)

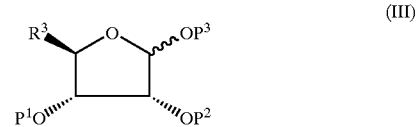

wherein $P^3$ represents a suitable protecting group for example $C_{1-3}$alkyl or acetyl, and $P^1$, $P^2$ and $R^3$ are as defined above, with a compound of formula (IV)

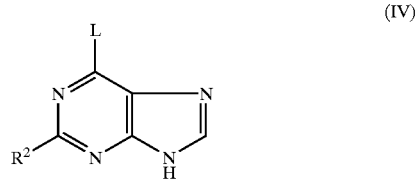

wherein L and $R^2$ are as defined above.

The reaction is conveniently carried out in a suitable solvent, such as acetonitrile in the presence of a silylating agent such as trimethylsilyl trifluoromethanesulfonate and a base such as diazabicyclo [5.4.0]undec-7-ene (DBU). Alternatively the compound of formula (IV) may first be silylated with a suitable silylating agent such as hexamethyldisilazane followed by reaction of the silylated intermediate with a compound of formula (III) and a suitable Lewis acid, for example trimethylsilyl trifluoromethanesulfonate in a suitable solvent such as acetonitrile.

Compounds of formula (IV) are either known in the art or may be prepared from known compounds using methods analogous to those used to prepare the known compounds of formula (IV).

Compounds of formula (III) may be prepared from alternative protected compounds by replacement of the alternate protecting groups with $P^1$ and $P^2$; for example when $P^1$ and $P^2$ represent acetyl, compounds of formula (III) may be prepared from compounds of formula (V) wherein $P^4$ and $P^5$ represent $C_{1-3}$ alkyl and $P^3$ is as defined above by acid catalysed removal of the alkylidine protecting group, e.g. with hydrogen chloride in methanol, followed by in situ acylation for example with acetic anhydride in the presence of a base such as pyridine, in a solvent such as dichloromethane.

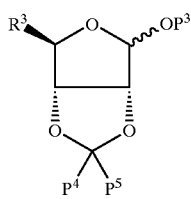

(V)

Compounds of formula (V) are known compounds or prepared by methods analogous to those used in the art to prepare the known compounds of formula V. It will be appreciated by a skilled person that the acetyl group in any of the compounds above could be replaced with any suitable protecting group, for example, other esters.

By analogous methods, compounds of formula (I) or (II) may also be prepared from compounds wherein alkylidene groups defined by $P^4$ and $P^5$ replace $P^1$ an $P^2$. This reaction represents an exchange of one protecting group for another and such reactions will be apparent to a person skilled in the art.

According to Route B, compounds of formula (II) may be prepared from 6-chloropurine riboside (VI) which is commercially available or prepared from inosine.

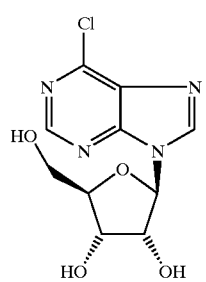

(VI)

The first stage of the process is to protect the 2', 3'-hydroxyl groups to produce compounds of formula (VII).

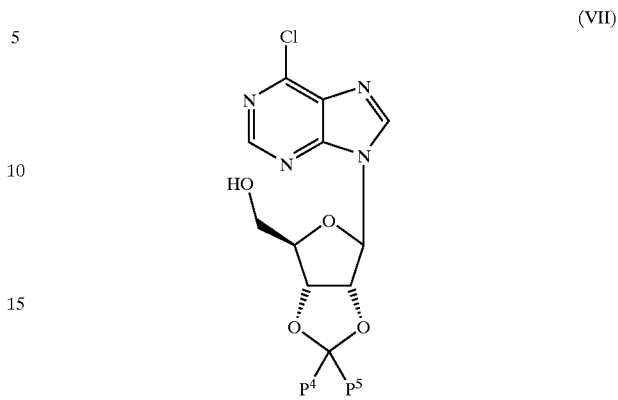

(VII)

wherein $P^4$ and $P^5$ are defined hereinabove. When the 2', 3'-hydroxyl groups are protected with an isopropylidine group ($P^4$ and $P^5$ represent methyl) this may be effected by the use of acetone and PTSA (para-toluene sulfonic acid) or by other standard procedures using dimethoxy propane apparent to a skilled person.

The compound of formula (VII) is then fluorinated in a single step using TsF (para-toluenesulfonyl fluoride) and TBAF (tetra-n-butylammonium fluoride in THF (tetrahydrofuran). This forms a compound of formula (VIII).

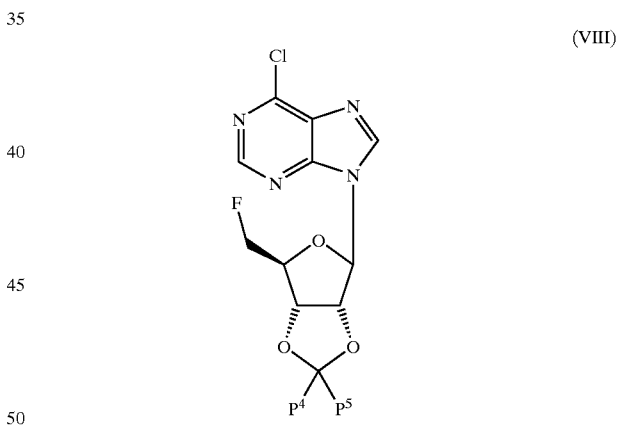

(VIII)

It will be apparent to a skilled person that the fluoroalkyl substituent at $R^3$ may be modified at this stage. Any $R^2$ substituent may also be introduced at an appropriate stage.

Finally the compound of formula (VIII) is deprotected by standard conditions e.g. acidic Dowex resin and the chlorine group is displaced by the group $R^1NH_2$ as described hereinabove to form a compound of formula (I).

According to a further process (C), compounds of formula (I) may be prepared using a purine-pyrimidine transferase enzyme system. This is demonstrated schematically below:

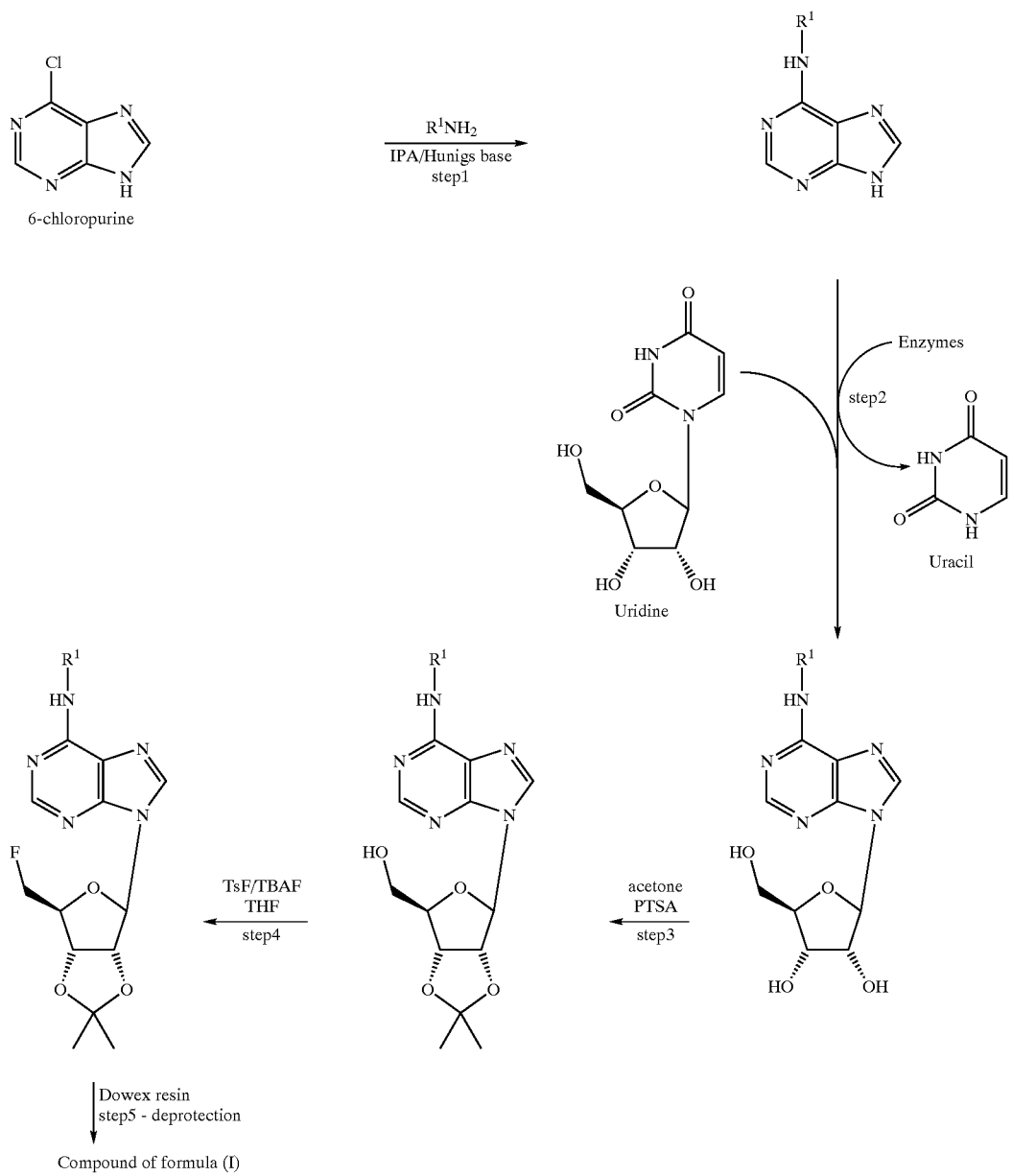

This enzyme system in step 2 transfers the purine ring onto the sugar ring of uridine. As shown in the reaction scheme, the group $R^1NH$— has already been introduced by standard methods but a skilled person would appreciate this could be added at any time during the reaction scheme.

Following step 2, the sugar ring is protected by $P^4$ and $P^5$ groups as described hereinabove, for example $P^4$ and $P^5$ represent methyl, followed by fluorination of the 5'-hydroxyl group. The compound is then deprotected to produce a compound of formula (I).

This reaction scheme is intended to demonstrate the use of the enzyme system. A skilled person would be able to adapt to produce compounds of formula (I) with alternate $R^2$ and $R^3$ groups. This would be standard chemistry apparent to a person skilled in the art.

A further process (D) comprises converting a compound of formula (I) into a different compound of formula (I) by modifying the $R^1$, $R^2$ or $R^3$ group therein. Certain compounds of formulae (II), (III), and (V) are novel intermediates and form a further aspect of the present invention.

Compounds of the formula $R^1NH_2$ are either known compounds or may be prepared from known compounds using conventional procedures with some exceptions indicated in the experimental section hereinbelow.

Specific optical isomers of a compound of formula (I) may be obtained by conventional methods for example, by synthesis from an appropriate asymmetric starting material using any of the processes described herein, or where appropriate by separation of a mixture of isomers of a compound of formula (I) by conventional means e.g by fractional crystallisation or chromatography.

In the general processes described above, the compound of formula (I) obtained may be in the form of a salt, conveniently into the form of a pharmaceutically acceptable salt. Where desired, such salts may be converted into the corresponding free bases using conventional methods.

Pharmaceutically acceptable acid addition salts of the compounds of formula (I) may be prepared by reacting a compound of formula (I) with an appropriate acid in the presence of a suitable solvent such as acetonitrile, acetone, chloroform, ethyl acetate or an alcohol (e.g. methanol, ethanol or isopropanol). Pharmaceutically acceptable base addition salts may be obtained in an analogous manner by treating a solution of a compound of formula (I) with a suitable base. Pharmaceutically acceptable salts may also be prepared from other salts, including other pharmaceutically acceptable salts of the compounds of formula (I), using conventional methods.

The invention is further illustrated by the following non-limiting Intermediates and Examples.

Standard HPLC conditions are as follows:
Standard Automated Preparative HPLC Column, Conditions & Eluent Automated preparative high performance liquid chromatography (autoprep. HPLC) was carried out using a Supelco® ABZ+5 μm 100 mm×22 mm i.d. column eluted with a mixture of solvents consisting of i) 0.1% formic acid in water and ii) 0.05% formic acid in acetonitrile, the eluent being expressed as the percentage of ii) in the solvent mixture, at a flow rate of 4 ml per minute. Unless otherwise stated the eluent was used as a gradient of 0–95% (ii) over 20 minutes.

LC/MS System

Two alternative Liquid Chromatography Mass Spectroscopy (LC/MS) systems were used:

System A

This system used an ABZ+PLUS, 3.3 cm×4.6 mm i.d. column, eluting with solvents: A—0.1% v/v formic acid+ 0.077 % w/v ammonium acetate in water; and B—95:5 acetonitrile:water+0.05% v/v formic acid, at a flow rate of 1 ml per minute. The following gradient protocol was used: 100% A for 0.7 mins; A+B mixtures, gradient profile 0–100% B over 3.5 mins; hold at 100% B for 3.5 mins; return to 100% A over 0.3 mins.

System B

This system used an ABZ+PLUS, 3.3 cm×2.0 mm i.d. column, eluting with solvents: A—0.1% v/v formic acid+ 0.077% w/v ammonium acetate in water; and B—95:5 acetonitrile:water+0.05% v/v formic acid, at a flow rate of 0.8 ml per minute. The following gradient protocol was used: A+B mixtures, gradient profile 0–100% B over 3.5 mins; hold at 100% B for 1.5 mins; return to 100% A over 0.5 mins.

Both systems used a micromass 'platform' spectrometer, with electrospray ionisation mode, positive and negative ion switching, mass range 80–1000 a.m.u.

HPLC System

The analytical HPLC system used an Inertsil® ODS2 150 mm×4.6 mm i.d. column, eluting with solvents: A—0.1% v/v phosphoric acid and B—95:5 acetonitrile:water+0.1% v/v phosphoric acid. The following gradient protocol was used with a flow rate of 1.0 mL/min: 100% A for 2 min; A+B mixtures, gradient profile 0–100% B over 40 min; hold at 100% B for 10 min.

Flash chromatography was carried out either on Merck silica gel (Merck 9385), or on pre-packed silica gel cartridges (Biotage).

Intermediate 1

β Anomer: Acetic Acid 4R-acetoxy-2S-fluoromethyl-5R-methoxy-tetrahydro-furan-3S-yl Ester α Anomer: Acetic Acid 4R-acetoxy-2S-fluoromethyl-5S-methoxy-tetrahydro-furan-3S-yl Ester (3aS,4S,6R,6aR)-4-Fluoromethyl-6-methoxy-2,2-dimethyl-tetrahydro-furo[3,4-d][1,3]dioxole (Sharma, Moheshwar; Li, Yi X.; Ledvina, Miroslav; Bobek, Miroslav. Nucleosides Nucleotides (1995), 14(9 & 10), 1831–52.) (4.0 g) was heated under reflux with conc. hydrochloric acid (0.8 ml) in methanol (140 ml) for 1.5 h. The solvent was evaporated, more methanol (120 ml) was added and heating under reflux continued overnight (16 h). The solvent was again evaporated in vacuo, fresh methanol (120 ml) added, and heating under reflux continued for 5 h. The solvent was evaporated in vacuo and the residue azeotroped with methanol (50 ml) to give the crude diol intermediate as a colourless oil (3.04 g). The crude diol was dissolved in dry dichloromethane (80 ml) and treated with pyridine (6.3 ml) acetic anhydride (5.5 ml; 5.85 mmol) and 4-dimethylaminopyridine (100 ml). The mixture was stirred at room temperature under nitrogen for 16 h, and the solvent was evaporated in vacuo to give a pale yellow oil (4.8 g). The oil was partitioned between dichloromethane and 8% aqueous sodium bicarbonate; the organic layers were washed with brine, dried ($MgSO_4$) and evaporated in vacuo to give a pale yellow oil (4.34 g). Purification by flash chromatography on silica gel (Biotage), eluting with ethyl acetate:cyclohexane 25:75 and 40:60, gave the title compound (α and β anomers).

β-anomer: Colourless oil (2.2 g)

TLC $SiO_2$ (Ethyl acetate:cyclohexane 1:2) Rf=0.4

α-anomer: Colourless oil (0.945 g)

TLC $SiO_2$ (Ethyl acetate:cyclohexane 1:2) Rf=0.2

Intermediate 2

Acetic Acid 4S-acetoxy-2R-(6-chloro-purin-9-yl)-5S-fluoromethyl-tetrahydro-furan-3R-yl Ester A suspension of 6-chloropurine (5.53 g) in hexamethyldisilazane (75 ml) and dry toluene (75 ml) was heated under reflux under nitrogen for 2 h. After cooling, the solvents were evaporated in vacuo and the residue co-evaporated with toluene (50 ml). The silylated purine thus obtained was dissolved in dry acetonitrile (75 ml) and acetic acid 4R-acetoxy-2S-fluoromethyl-5R-methoxy-tetrahydro-furan-3S-yl ester (3.03 g) added, followed by trimethylsilyl trifluoromethanesulphonate (5.0 ml). The solution was heated at 90° C. for 2 h, cooled, and poured into 8% aqueous sodium bicarbonate (200 ml). The mixture was extracted with ethyl acetate and the extracts dried ($Na_2SO_4$) and evaporated in vacuo. Further crude product was obtained from acetic acid 4R-acetoxy-2S-fluoromethyl-5S-methoxy-tetrahydro-furan-3S-yl ester (5.56 g) and 6-chloropurine (5.53 g) as described above. The crude products were combined and purified by flash chromatography on silica gel (Merck 9385), eluting with ether, to afford the title compound as a white solid (9.17 g).

TLC $SiO_2$ (Ether) Rf=0.2

Intermediate 3

Acetic Acid 4S-acetoxy-5S-fluoromethyl-2R-[6-(tetrahydro-pyran-4-ylamino)-purin-9-yl]-tetrahydro-furan-3R-yl Ester A solution of acetic acid 4S-acetoxy-2R-(6-chloro-purin-9-yl)-5S-fluoromethyl-tetrahydro-furan-3R-yl ester (3.03 g) in isopropanol (120 ml) was treated with diisopropylethylamine (8.4 ml) and 4-aminotetrahydropyran hydrochloride (Johnston, Thomas P.; McCaler, George S.; Opliger, Pamela S.; Laster, W. Russell; Montgomery, John A. Kettering-Meyer Lab., J. Med. Chem. (1971), 14(7), 600–14.) (3.26 g), and the mixture was heated under reflux under nitrogen for 8 h. The solution was cooled and the solvent evaporated in vacuo. The residue was treated with 8% sodium bicarbonate (150 ml) and extracted with ethyl acetate. The extracts were dried (Na$_2$SO$_4$) and evaporated in vacuo to give the title compound as a foam (3.67 g).

LC/MS (System A): R$_t$=3.81 min

Intermediate 4 (PCT Int. Appl., WO 9507921 A1 950323.)

Acetic Acid 4S-acetoxy-2R-(2,6-dichloro-purin-9-yl)-5S-fluoromethyl-tetrahydro-furan-3R-yl Ester 2,6-Dichloropurine (6.1 g) was heated with hexamethyldisilazane (112 ml) at 130° C. with stirring under nitrogen for 2 h. The mixture was evaporated in vacuo to give a white solid, which was azeotroped with dry toluene (80 ml). The residue was treated with a solution of acetic acid 4R-acetoxy-2S-fluoromethyl-5R-methoxy-tetrahydro-furan-3S-yl ester (Intermediate 1-β anomer) (2.5 g) in dry acetonitrile (100 ml) followed by trimethylsilyl trifluoromethanesulphonate (6.63 ml) and the mixture was heated under reflux for 2 h. The mixture was partitioned between saturated aqueous sodium bicarbonate and dichloromethane and the organic layers washed with brine, dried (MgSO$_4$) and evaporated in vacuo to give a brown gum (4.6 g). Purification by flash chromatography on silica gel (Merck 9385), eluting with ethyl acetate:cyclohexane 40:60, gave the title compound as a white foam (2.67 g; 64%).

TLC SiO$_2$ (Ethyl acetate:cyclohexane 2:1) Rf =0.55.

Intermediate 5

Acetic Acid 4S-acetoxy-2R-(6-chloro-2-methyl-purin-9-yl)-5S-fluoromethyl-tetrahydro-furan-3R-yl Ester 6-Chloro-2-methylpurine (Bourguignon, Jean-Jacques; Desaubry, Laurent; Raboisson, Pierre; Wermuth, Camille-Georges; Lugnier, Claire. Bourguignon, Jean-Jacques; Desaubry, Laurent; Raboisson, Pierre; Wermuth, Camille-Georges; Lugnier, Claire. Laboratoire de Pharmacochimie Moleculaire, Centre de Neurochimie, Strasbourg, 67084, Fr. J. Med. Chem. (1997), 40(12), 1768–1770. (202 mg) was heated at 80° C. with hexamethyldisilazane (2 ml) and dry toluene (3 ml) for 24 h. Dry toluene (5 ml) was added, the solvent was evaporated in vacuo, and the residue azeotroped with further dry toluene (5 ml). A solution of acetic acid 4R-acetoxy-2S-fluoromethyl-5R-methoxy-tetrahydro-furan-3S-yl ester (98 mg) in dry acetonitrile (5 ml) was added to the crude silylated purine, followed by trimethylsilyl trifluoromethanesulphonate (0.26 ml). The mixture was heated under reflux for 4 h, allowed to cool, and partioned between saturated aqueous sodium bicarbonate (5 ml) and dichloromethane (40 ml). The organic layer was washed with water, dried (MgSO$_4$) and evaporated in vacuo to give the crude product. Purification by flash chromatography on silica gel (Merck 9385), eluting with cyclohexane:ethyl acetate (1:1), gave the title compound as a white solid (109 mg).

Mass spectrum m/z 387 (MH$^+$)

Intermediate 6

Acetic Acid 4S-acetoxy-5S-fluoromethyl-2R-[2-methyl-6-(tetrahydro-pyran-4-ylamino)-purin-9-yl]-tetrahydro-furan-3R-yl Ester A solution of acetic acid 4S-acetoxy-2R-(6-chloro-2-methyl-purin-9-yl)-5S-fluoromethyl-tetrahydro-furan-3R-yl ester (108 mg), 4-aminotetrahydropyran hydrochloride (153 mg) and diisopropylethylamine (0.13 ml) in isopropanol (10 ml) was heated at 80° for 72 h. The solvent was evaporated in vacuo to give a brown semi-solid residue. Purification by flash chromatography on silica gel (Merck 9385), eluting with ethyl acetate:cyclohexane 1:1, ethyl acetate, and ethyl acetate:ethanol 10:1, gave the title compound (61 mg). Mass spectrum m/z 452 (MH$^+$)

Intermediate 7

Acetic Acid 4R,5-diacetoxy-2-trifluoromethyl-tetrahydro-furan-3S-yl Ester (3aR,6S,6aS)-2,2-Dimethyl-6-trifluoromethyl-tetrahydro-furo[3,4-d][1,3]dioxol-4-ol (Munier, Pascal; Picq, Dominique; Anker, Daniel. Munier, Pascal; Picq, Dominique; Anker, Daniel. Lab. Chim. Org., Univ. Claude Bernard, Villeurbanne, 69622, Fr. Tetrahedron Lett. (1993), 34(51), 8241–4.) (1.07 g) was dissolved in 9:1 trifluoroacetic acid:H$_2$O (15 ml) and the solution was stirred at 22° C. for 4 h. The solution was concentrated in vacuo, followed by repeated coevaporation with toluene to give a clear, colourless gum. The gum was dissolved in dry pyridine (30 ml), acetic anhydride (8.99 ml) was added, and the resulting solution was stirred at 22° C. under N$_2$ for 3 days. The pyridine and excess acetic anhydride were evaporated in vacuo, followed by repeated coevaporation with toluene to give a dark brown oil. Purification by flash column chromatography on silica gel (Merck 9385) eluting with cyclohexane: ethyl acetate 1:1, gave the title compound as a pale yellow gum (1.37 g).

TLC SiO$_2$ (Ethyl acetate) Rf=0.9.

Intermediate 8

Acetic Acid 4S-acetoxy-2R-(2,6-dichloro-purin-9-yl)-5S-trifluoromethyl-tetrahydro-furan-3R-yl Ester Acetic acid 4R,5-diacetoxy-2-trifluoromethyl-tetrahydro-furan-3S-yl ester (1.09 g) was dissolved in anhydrous acetonitrile (5 ml) and 2,6-dichloropurine (0.788 g) was added, followed by 1,8-diazabicyclo[5.4.0]undec-7-ene (DBU) (0.676 ml) and trimethylsilyl trifluoromethanesulphonate (0.94 ml) (TMSOTf). The resulting solution was stirred at 22° C. under nitrogen for 16 h. Further 2,6-dichloropurine (200 mg) was added, followed by DBU (0.17 ml) and TMSOTf (0.24 ml) and the mixture was stirred at 22° C. under nitrogen for 4 days, followed by heating under reflux for 4 h. The mixture was cooled, and partitioned between ethyl acetate and water. The aqueous layer was extracted with ethyl acetate, and the combined organic extracts were dried (MgSO$_4$), and concentrated in vacuo to give a brown gum. Purification by flash column chromatography on silica gel (Merck 9385), eluting with 1:1 cyclohexane:ethylacetate, gave the title compound as a pale yellow foam (1.30 g).

TLC SiO$_2$ (Ethyl acetate) Rf=0.6.

Intermediate 9

Acetic Acid 4S-acetoxy-2R-[2-chloro-6-(tetrahydro-pyran-4-ylamino)-purin-9-yl]-5S-trifluoromethyl-tetrahydro-furan-3 R-yl Ester Acetic acid 4S-acetoxy-2R-(2,6-dichloro-purin-9-yl)-5S-trifluoromethyl-tetrahydro-furan-3R-yl ester (177 mg) was heated at 60° C. with 4-aminotetrahydropyran hydrochloride (110 mg) and diisopropylethylamine (0.17 ml) in isopropanol (5 ml) for 2 days. The solvent was evaporated in vacuo and the residue purified by flash chromatography on silica gel (Merck 9385), eluting with ethyl acetate:cyclohexane 2:1, to give the title compound as a white foam (0.146 g).

Mass Spectrum m/z 508 (MH$^+$).

Intermediate 10

(3aS,4S,6R,6aR)-4-(1,1-Difluoro-ethyl)-6-methoxy-2,2-dimethyl-tetrahydro-furo[3,4-d][1,3]dioxole A solution of 1-(6R-methoxy-2,2-dimethyl-tetrahydro-(3aS,6aR)-furo[3,4-d][1,3]dioxol-4S-yl)-ethanone (Hampton, Alexander; Perini, Florian; Harper, Peter J. Fox Chase Cent. Hampton, Alexander; Perini, Florian; Harper, Peter J. Fox Chase Cent. Cancer Med. Sci., Inst. Cancer Res., Philadelphia, Pa., USA. Carbohydr. Res. (1974), 37(2), 359–67.) (6.53 g) in dichloromethane (200 ml) was treated with diethylaminosulphur trifluoride (10.4 ml) and the mixture was stirred at 22° C. for 5 days. The solution was added carefully to 2M aqueous sodium carbonate (200 ml), the mixture carefully shaken, the organic phase collected, and the aqueous layer further extracted with dichloromethane. The combined organic layers were dried ($Na_2SO_4$) and evaporated in vacuo. The residue was purified by flash chromatography on silica gel (Merck 9385) eluting with cyclohexane and cyclohexane:ether (19:1–9:1) to give the title compound as a pale yellow oil (4.72 g).

NMR ($CDCl_3$) 5.08δ(1H,brs,CH), 4.95δ(1H,brd,CH), 4.59δ(1H,d,CH), 4.21δ(1H,dd,CH,JF—C—CH 6.22 Hz, 3.39δ(3H,s,OMe), 1.68δ(3H,t,JF—C—CH$_3$), 1.5, 1.33δ(2× 3(2×3H,2×s,2×CH$_3$).

Intermediate 11

(β Anomer): rel-Acetic Acid 4R,5S-diacetoxy-2S-(1,1-difluoro-ethyl)-tetrahydro-furan-3S-yl Ester (α Anomer): rel-Acetic Acid 4R,5R-diacetoxy-2S-(1,1-difluoro-ethyl)-tetrahydro-furan-3S-yl Ester (3aS,4S,6R,6aR)-4-(1,1-Difluoro-ethyl)-6-methoxy-2,2-dimethyl-tetrahydro-furo[3,4-d][1,3]dioxole (4.71 g) was dissolved in acetic acid:water (4:1, 125 ml) and the mixture heated under reflux under nitrogen for 18 h. The solvents were removed in vacuo and the residue was co-evaporated twice with toluene, dissolved in dichloromethane (70 ml), and treated with pyridine (8 ml), 4-dimethylaminopyridine (30 mg) and acetic anhydride (7 ml). The dark solution was allowed to stand for 41 h. The solvents were removed in vacuo and the residue co-evaporated twice with toluene. The residue was partitioned between 8% aqueous sodium bicarbonate and dichloromethane. The organic extracts were dried ($Na_2SO_4$), and evaporated in vacuo and the residue purified by flash chromatography on silica gel (Merck 9385), eluting with cyclohexane:ether (1:1–2:3–1:4), to give the title compound (β anomer): 2.51 g (41%); and the title compound (α anomer): 2.13 g (35%).

(β anomer): TLC $SiO_2$ (Ether) Rf=0.58.

(α anomer): TLC $SiO_2$ (Ether) Rf=0.51.

Intermediate 12

Acetic Acid 4S-acetoxy-2R-(6-chloro-purin-9-yl)-5S-(1,1-difluoro-ethyl)-tetrahydro-furan-3R-yl Ester 6-chloropurine (1.52 g), hexamethyldisilazane (10 ml) and toluene (50 ml) were heated under reflux under nitrogen for 2 h. The solvents were removed in vacuo, and rel-Acetic acid 4R,5R-diacetoxy-2S-(1,1-difluoro-ethyl)-tetrahydro-furan-3S-yl ester (2.31 g) was added in dry acetonitirle (50 ml), followed by 1,8-diazabicyclo[5.4.0]undec-7-ene (2.0 ml, 13.4 mmol) and trimethylsilyl trifluoromethanesulphonate (4.8 ml). The mixture was stirred at 22° C. for 17 h, then heated at 85° C. for 90 min. The mixture was poured into 8% aqueous sodium bicarbonate and extracted with ethyl acetate. The organic extracts were dried ($Na_2SO_4$) and evaporated in vacuo, and the residue purified by flash chromatography on silica gel (Merck 9385) eluting with cyclohexane ether (1:1) and ether to give the title compound as a pale yellow gum (2.49 g).

TLC $SiO_2$ (Ether) Rf=0.30

Intermediate 13

2-(2S-Hydroxy-(S)-cyclopentyl)-isoindole-1,3-dione (1S,2S)-2-Amino-cyclopentanol hydrochloride (1.20 g) was dissolved in a solution of sodium methoxide (497 mg) in methanol (10 ml), filtered and evaporated in vacuo. The residue was dissolved in toluene (30 ml) and phthalic anhydride (1.55 g) added, and the mixture heated under reflux for 24 h. After cooling, ethyl acetate was added and the mixture filtered. The filtrate was evaporated in vacuo and the residue purified by flash chromatography over silica (40 g) eluting with cyclohexane-ethyl acetate (2:1) to afford the title compound as a colourless solid (1.08 g).

Mass spectrum m/z 232 ($MH^+$)

Intermediate 14

2-(2S-Fluoro-(S)-cyclopentyl)-isoindole-1,3-dione 2-(2S-hydroxy-(S)-cyclopentyl)-isoindole-1,3-dione (3.42 g) was dissolved in dry dichloromethane (55 ml) and diethylaminosulfur trifluoride (3.43 ml) added, and the solution stirred under reflux under nitrogen for 72 h. The solution was poured carefully into 8% sodium bicarbonate solution (100 ml) and the organic phase separated. The aqueous phase was further extracted with dichloromethane and the combined organic layers dried ($MgSO_4$) and evaporated in vacuo. The residue was purified by flash chromatography over silica (100 g) eluting with cyclohexane-ethyl acetate (1:1) to give the title compound as a cream powder (1.25 g).

Mass spec m/z 234 ($MH^+$), 251 ($MNH_4^+$)

Intermediate 15

(1S,2S)-2-Fluorocyclopentylamine hydrochloride 2-(2S-fluoro-(S)-cyclopentyl)-isoindol-1,3-dione (6.75 g), hydrazine hydrate (1.55 ml) and ethanol (200 ml) were treated with water (1.55 ml) and heated under reflux for 4 h. The mixture was cooled to 20° C., filtered and the filtrate treated with conc. hydrochloric acid to pH1. The solution was evaporated in vacuo and taken up in water, filtered, and the filtrate evaporated in vacuo. The residue was recrystallised (with hot filtration) from ethyl acetate-methanol (3:1) to afford the title compound as an off-white solid (2.59 g).

NMR δ(DMSO) 8.3 (3H, brs, —$NH_3^+$), 5.04, (1H, dm, C HF, J F—C—H, 52 Hz), 3.49 (1H, brdm, CH, J F—C—C—H 20 Hz), and 2.2–1.4 (6 Hm, 333 $CH_2$).

EXAMPLE 1

5'-Deoxy-5'-fluoro-N-(tetrahydro-pyran-4-yl)-adenosine

A solution of acetic acid 4S-acetoxy-5S-fluoromethyl-2R-[6-tetrahydro-pyran-4-yl amino)-purin-9-yl]-tetrahydro-furan-3R-yl ester (3.67 g) in methanol (120 ml) was treated with a solution of potassium carbonate (3.50 g) in water (ca. 15 ml) and the mixture was stirred at 23° C. for 17 h. The resulting solution was applied directly onto silica gel (20 g) and purified by flash chromatography on silica gel (Merck 9385), eluting with dichloromethane:methanol (10:1), to give the title compound as a colourless solid (2.16 g).

Recrystallisation from ethanol (75 ml) gave the title compound as a colourless solid (1.48 g).

LC/MS (System A): $R_t$=3.25 min.

Mass spectrum m/z 360 ($MH^+$)

EXAMPLE 2

5'-Deoxy-5'-fluoro-2-methyl-N-(tetrahydro-pyran-4-yl)-adenosine

Acetic acid 4S-acetoxy-5S-fluoromethyl-2R-[2-methyl-6-(tetrahydro-pyran-4-ylamino)-purin-9-yl]-tetrahydro-furan-3R-yl ester (56 mg) was stirred with potassium carbonate (42 mg) in methanol (2 ml) and water (2 ml) at 22° C. for 24 h. The solvent was evaporated in vacuo, and the residue purified by flash chromatography on silica gel (Merck 9385), eluting with dichloromethane:ethanol:880 ammonia (100:10:1), to give the title compound as a white solid (44 mg).

TLC $SiO_2$ ($CH_2Cl_2$:EtOH:880 ammonia, 100:10:1) Rf=0.25.

Mass spectrum m/z 368 ($MH^+$)

EXAMPLE 3

2-Chloro-5'-deoxy-5'-fluoro-N-(tetrahydro-pyran-4-yl)-adenosine

Acetic acid 4S-acetoxy-2R-(2,6-dichloro-purin-9-yl)-5S-fluoromethyl-tetrahydro-furan-3R-yl ester (50 mg) was heated at 55–58° C. with 4-aminotetrahydropyran hydrochloride (33 mg) and diisopropylethylamine (0.125 ml) in isopropanol (5 ml) for 21 h. On cooling to room temperature, methanolic ammonia (4 ml) was added, and the mixture was allowed to stand at room temperature (22° C.) overnight (16 h). The mixture was evaporated to dryness in vacuo to give the crude product which was purified by solid phase extraction (5 g, Varian Mega Bondelut cartridge, aminopropyl bonded phase, eluting with (i) $CHCl_3$, (ii) acetone, to give the title compound (47 mg).

TLC $SiO_2$ ($CH_2Cl_2$:MeOH 9:1) Rf=0.5

Mass spectrum m/z 388 ($MH^+$)

EXAMPLE 4

(2R,3 R,4S,5S)-2-[2-Chloro-6-(tetrahydro-pyran-4-ylamino)-purin-9-yl]-5-trifluoromethyl-tetrahydro-furan-3,4-diol Acetic acid 4S-acetoxy-2R-[2-chloro-6-(tetrahydro-pyran-4-ylamino)-purin-9-yl]-5S-trifluoromethyl-tetrahydro-furan-3R-yl ester (141 mg) was stirred at room temperature with potassium carbonate (115 mg) in 2:1 methanol:water (6 ml) for 17 h. The solvent was evaporated in vacuo to give a yellow solid (0.274 g). Purification by flash chromatography on silica gel (Merck 9385), eluting with ethyl acetate and ethyl acetate:methanol 9:1, gave the title compound as a white solid (96 mg).

TLC $SiO_2$ (Ethyl acetate) Rf=0.25.

Mass Spectrum m/z 424 ($MH^+$).

EXAMPLE 5

(2R,3R,4S,5S)-2-[6-(Bicyclo[2.2.1]hept-2-ylamino)-purin-9-yl]-5-(1,1-difluoro-ethyl)-tetrahydro-furan-3,4-diol Acetic acid 4S-acetoxy-2R-(6-chloro-purin-9-yl)-5S-(1,1-difluoro-ethyl)-tetrahydro-furan-3R-yl ester (70 mg) was heated at 80–85° C. with (±)-endo-norbornylamine hydrochloride and N,N-diisopropylethylamine (0.18 ml) in isopropanol (5 ml) for 24 h. The solvent was evaporated to Ca 1 ml volume, methanolic ammonia (3 ml) added, and the mixture was allowed to stand for 17 h. The solvent was evaporated and the residue purified by solid phase extraction (Varian Bondelut cartridge, aminopropyl bonded phase) eluting with chloroform (to elute excess amine) followed by ethyl acetate:methanol 9:1, to give the title compound (0.025 g).

Mass Spectrum m/z 396 ($MH^+$).

NMR (MeOD) 8.22δ(1$\underline{H}$,s,heterocyclic CH), 8.17δ(1$\underline{H}$,s,heterocyclic CH), 6.08δ(1$\underline{H}$,d,CH), 4.64δ(1$\underline{H}$,t,CH), 4.49δ(1$\underline{H}$,dd,CH), 4.40δ(1$\underline{H}$,vbrs,CH), 4.15δ(1$\underline{H}$,ddd,CH) JF—C—C$\underline{H}$,7,17$H_3$), 2.57δ(1$\underline{H}$,brt,CH), 2.3–2.08δ(2$\underline{H}$,brt+m,2×CH), 1.8–1.5δ(6$\underline{H}$,t+3×CH), 1.5–1.3δ(3$\underline{H}$,m,3×CH), 1.04δ(1$\underline{H}$,ddd,CH).

By analogous methods, the following examples were synthesised:

EXAMPLE 6

2-Chloro-5-deoxy-5'-fluoro-N-(2R-fluoro-cyclopent-(R)-yl)-adenosine

Prepared from
Intermediate 4 (as Example 3)

LC/MS (system A): $R_t$=4.01 min

Mass spectrum m/z 390 ($MH^+$)

EXAMPLE 7

2-Chloro-5'-deoxy-5'-fluoro-N-(2S-hydroxy-cyclopent-(S)-yl)adenosine

Prepared from Intermediate 4 as (Ex 3)

LC/MS (system A): $R_t$=3.55 min

Mass spectrum m/z 388 ($MH^+$).

EXAMPLE 8

N-(endo-Bicyclo[2.2.1]hept-2-yl)-2-chloro-5'-deoxy-5'-fluoro-adenosine

Prepared from Intermediate 4 (as Ex.3)

LC/MS (system A): $R_t$=4.32 min

Mass spectrum m/z 398 ($MH^+$)

EXAMPLE 9

4-[2-Chloro-9-(5S-fluoromethyl-3R,4S-dihydroxy-tetrahydro-furan-2R-yl)-9H-purin-6-ylamino]-piperidine-1-carboxylic acid ethyl ester From Intermediate 4 (as Ex.3)

LC/MS (system A): $R_t$=3.90 min

Mass spectrum m/z 459 ($MH^+$)

EXAMPLE 10

1-{4-[2-Chloro-9-(5S-fluoromethyl-3R,4S-dihydrox-tetrahydro-furan-2R-yl)-9H-purin-6-ylamino]-piperidin-1-yl}-ethanone From Intermediate 4 (as Ex.1)

LC/MS (system A): $R_t$=3.67 min

Mass spectrum m/z 429 ($MH^+$)

EXAMPLE 11

N-(endo-Bicyclo[2.2.1]hept-2-yl)-5'-deoxy-5'-fluoro-adenosine

From Intermediate 2 (as Ex.1)
LC/MS (system A): $R_t$=4.05 min
Mass spectrum m/z 364 (MH$^+$)

EXAMPLE 12

N-(exo-Bicyclo[2.2.1]hept-2-yl)-5'-deoxy-5'-fluoro-adenosine

From Intermediate 2 (as Ex.1)
Mass spectrum m/z 364 (MH$^+$)
HPLC $R_t$=14.8 min

EXAMPLE 13

5'-Deoxy-5'-fluoro-N-(2S-hydroxy-cyclopent-(S)-yl)-adenosine

From Intermediate 2 (as Ex.1)
Mass spectrum m/z 354 (MH$^+$)
HPLC $R_t$=10.3 min

EXAMPLE 14

4-[9-(5S-Fluoromethyl-3R,4S-dihydroxy-tetrahydro-furan-2R-yl)-9H-purin-6-ylamino]-piperidine-1-carboxylic acid ethyl ester From Intermediate 2 (as Ex.1)
Mass spectrum m/z 425 (MH$^+$)
HPLC $R_t$=14.0 min

EXAMPLE 15

2-Chloro-5'-deoxy-N-(1,1-dioxo-hexahydro-1.delta.6-thiopyran-4-yl)-5'-fluoro-adenosine From Intermediate 4 (as Ex.3)
LC/MS (system A): $R_t$=3.66 min
Mass spectrum m/z 436 (MH$^+$)

EXAMPLE 16

2-Chloro-5'-deoxy-N-(2,3-dihydroxy-propyl)-5'-fluoro-adenosine

From Intermediate 4 (as Ex.3)
LC/MS (system A):
$R_t$=3.07 min
Mass spectrum m/z 378 (MH$^+$)

EXAMPLE 17

(2R,3R,4S,5S)-2-[6-(Cyclopropylmethyl-amino)-purin-9-yl]-(1,1-difluoro-ethyl)-tetrahydro-furan-3,4-diol From Intermediate 12 (as Ex.5)
Mass spectrum m/z 356 (MH$^+$)
LC/MS (system A): $R_t$=3.73 min

EXAMPLE 18

2-[9-(5S-Fluoromethyl-3R,4R-dihydroxy-tetrahydro-furan-2R-yl)-9H-purin-6-ylamino]-ethanesulfonic acid methylamide From Intermediate 2 (as Ex.1)
Mass spectrum m/z 391 (MH$^+$)
HPLC $R_t$=10.1 min

EXAMPLE 19

5'-Deoxy-5'-fluoro-N-(2,2-dimethyl-propyl)-adenosine

From Intermediate 2 (as Ex.1)
LC/MS (system A): $R_t$=4.26 min
Mass spectrum m/z 340 (MH$^+$)

EXAMPLE 20

N-tert-Butyl-5'-deoxy-5'-fluoro-adenosine

From Intermediate 2 (as Ex.1)
LC/MS (system A): $R_t$=4.29 min
Mass spectrum m/z 326 (MH$^+$)

EXAMPLE 21

5'-Deoxy-5'-fluoro-N-(tetrahydro-thiopyran-4-yl)-adenosine

From Intermediate 2 (as Ex.1)
LC/MS (system A): $R_t$=4.09 min
Mass spectrum m/z 370 (MH$^+$)

EXAMPLE 22

2-Chloro-5'-deoxy-5'-fluoro-N-isobutyl-adenosine

From Intermediate 4 (as Ex.3)
LC/MS (system A): $R_t$=4.61 min
Mass spectrum m/z 360 (MH$^+$)

EXAMPLE 23

2-Chloro-5'-deoxy-5'-fluoro-N-(1-methanesulfonyl-piperidin-4-yl)-adenosine

From Intermediate 4 (as Ex.3)
LC/MS (system A): $R_t$=4.22 min
Mass spectrum m/z 465 (MH$^+$)

EXAMPLE 24

2-Chloro-5'-deoxy-N-(2,2-dimethyl-propyl)-5'-fluoro-adenosine

From Intermediate 4 (as Ex.3)
LC/MS (system A): $R_t$=4.77 min
Mass spectrum m/z 374 (MH$^+$)

EXAMPLE 25

N-(exo-Bicyclo[2.2.1]hept-2-yl)-2-chloro-5'-deoxy-5'-fluoro-adenosine

From Intermediate 4 (as Ex.3)
LC/MS (system A): $R_t$=4.92 min
Mass spectrum m/z 398 (MH$^+$)

EXAMPLE 26

4-[2-Chloro-9-(5S-fluoromethyl-3R,4S-dihydroxy-tetrahydro-furan-2R-yl)-9H-purin-6-ylamino]-piperidine-1-carboxylic acid butyl ester From Interm. 4 (as Ex.3)
LC/MS (system A): $R_t$=4.84 min
Mass spectrum m/z 487 (MH$^+$)

EXAMPLE 27

5N-Deoxy-N-((1-dioxo-hexahydro-1.delta.6-thiopyran-4-yl)-5'fluoro-adenosine

From Intermediate 2 (as Ex.1)

LC/MS (system A): $R_t$=3.64 min

Mass spectrum m/z 402 (MH$^+$)

EXAMPLE 28

N-(4-Chloro-2-fluoro-phenyl)-5'-deoxy-5'-fluoro-adenosine

From Intermediate 2 (as Ex.1)

Mass spectrum m/z 398 (MH$^+$)

LC/MS (system A): $R_t$=4.03 min

EXAMPLE 29

4-[2-Chloro-9-(5S-fluoromethyl-3R,4S-dihydroxy-tetrahydro-furan-2R-yl)-9H-purin-6-ylamino]-piperidine-1-carboxylic acid ethylamide From Intermediate 4 (as Ex.3)

LC/MS (system A): $R_t$=4.04 min

Mass spectrum m/z 458 (MH$^+$)

Reporter Gene Experiments

Agonist activity was measured in Chinese hamster ovary (CHO) cells containing the CRE/SPAP/HYG (CRE=cyclic AMP response element; HYG=hygromycin resistance; SPAP=secreted placental alkaline phosphatase) reporter gene elements, which upon stimulation of cAMP levels produced SPAP. A cell line was used, which was stably transfected with either the human adenosine A1 receptor or the human adenosine A3 receptor in addition to the above elements. Cells were plated out in 96-well plates in culture medium and incubated at 37° C. for 1 hour. For measurement of potency, agonists were added to the appropriate wells at a concentration range of approximately $10^{-10}$–$10^{-5}$M. 15 Min later, cAMP levels were stimulated by addition of a maximal concentration of forskolin. All cells were then incubated for a further 5 hours at 37° C., and cooled to room temperature, after which a substrate for the phosphatase (para-nitrophenol phosphate, pNPP), which is converted by SPAP to a coloured reagent) was then added and the 96-well plates were read in a plate reader. From these readings, the concentration-dependence of the inhibition by the agonist for forskolin-stimulated SPAP production can be calculated. One of the agonists tested on each 96-well plate was the standard non-selective agonist, N-ethylcarboxamidoadenosine (NECA), and the potency of all test agonists is expressed relative to that of the NECA standard.

(ECR=equipotent concentration ratio relative to NECA= 1)

TABLE 1

Biological Data: A1, A3 Receptor, Reporter Gene Assay ECR

| Example | A1 | A3 |
|---|---|---|
| 1 | 1.9 | >226.00 |
| 2 | 11.8 | >226.00 |
| 3 | 2.41 | >139.00 |

TABLE 1-continued

Biological Data: A1, A3 Receptor, Reporter Gene Assay ECR

| Example | A1 | A3 |
|---|---|---|
| 4 | 190.10 | — |
| 5 | 7.14 | >257.00 |
| 6 | 0.91 | >156.00 |
| 7 | 0.45 | >91.00 |
| 8 | 0.21 | >91.00 |
| 9 | 3.00 | >129.00 |
| 10 | 66.80 | >162.00 |
| 11 | 0.47 | >152.00 |
| 12 | 0.54 | >152.00 |
| 13 | 1.47 | >152.00 |
| 14 | 1.68 | >435.00 |
| 15 | 9.16 | >435.00 |
| 16 | 7.29 | >240.00 |
| 17 | 22.30 | >353.00 |
| 18 | 0.71 | >353.00 |
| 19 | 3.51 | >353.00 |
| 20 | 8.17 | >353.00 |
| 21 | 1.64 | >353.00 |
| 22 | 3.30 | >145.00 |
| 23 | 11.20 | 48.90 |
| 24 | 7.83 | >233.00 |
| 25 | 0.78 | >151.00 |
| 26 | 4.50 | >233.00 |
| 27 | 6.20 | >162.00 |
| 28 | 2.05 | >170.00 |
| 29 | 51.60 | >236.00 |

What is claimed is:

1. A compound of formula (I) which is an agonist at the adenosine A$_1$ receptor

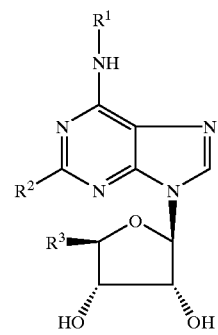

wherein

R$^2$ represents C$_{1-3}$ alkyl, halogen or hydrogen;

R$^3$ represents a fluorinated straight or branched alkyl group of 1–6 carbon atoms;

R$^1$ represents a group selected from the group consisting of:

(1) -(alk)$_n$—(C$_{3-7}$) cycloalkyl or -(alk)$_n$—(C$_{3-7}$) bridged cycloalkyl, wherein either group may be optionally substituted by one or more substituents selected from the group consisting of OH, halogen, and —(C$_{1-3}$) alkoxy, wherein (alk) represents C$_{1-3}$ alkylene and n represents 0 or 1;

(2) an aliphatic heterocyclic group of 4 to 6 membered rings containing at least one heteroatom selected from the group consisting of O, N and S, optionally substituted by one or more substituents selected from the group consisting of —(C$_{1-3}$)alkyl, —CO$_2$—(C$_{1-4}$) alkyl, —CO(C$_{1-3}$alkyl), —S(=O)$_n$—(C$_{1-3}$alkyl), —CONR$^a$R$^b$ (wherein R$^a$ and R$^b$ independently represent H or C$_{1-3}$alkyl) and =O; and where there is a sulfur atom in the heterocyclic ring, said sulfur is optionally substituted by $(=O)_n$, where n is 1 or 2;

(3) straight or branched $C_{7-12}$ alkyl, optionally including one or more O, $S(=O)_n$ (where n is 0, 1 or 2), or N groups substituted within the alkyl chain, wherein said alkyl is optionally substituted by one or more of the following groups, halogen, hydroxy or $NR^aR^b$ wherein $R^a$ and $R^b$ both represent $C_{1-3}$alkyl or hydrogen;

(4) a fused bicyclic aromatic ring

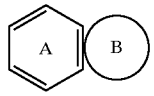

wherein B represents a 5 or 6 membered heterocyclic aromatic group containing 1 or more ), N or S atoms, wherein the bicyclic ring is attached to the nitrogen atom of formula (I) via a ring atom of ring A and ring B is optionally substituted by —$CO_2$—($C_{1-3}$ alkyl);

(5) a phenyl group optionally substituted by one or more substituents selected from the group consisting of:
-halogen, —$SO_3H$, -(alk)$_n$—OH, -(alk)$_n$-cyano, —(O)$_n$—($C_{1-6}$)alkyl (optionally substituted by one or more halogens), -(alk)$_n$-nitro, —(O)$_m$-(alk)$_n$—$CO_2R^c$, -(alk$_n$)—$CONR^cR^d$, -(alk)$_n$—$COR^c$, -(alk)$_n$—$SOR^e$, -(alk)$_n$—$SO_2R^e$, -(alk)$_n$—$SO_2NR^cR^d$, -(alk)$_n$—$OR^c$, -(alk)$_n$—(CO)$_m$—$NHSO_2R^e$, -(alk)$_n$—$NHCOR^c$, and -(alk)$_n$—$NR^cR^d$ wherein m and n are 0 or 1 and alk represents a $C_{1-6}$ alkylene group or $C_{2-6}$ alkenyl group; and (6) a phenyl group substituted by a 5 or 6 membered heterocyclic aromatic group, said heterocyclic aromatic group optionally being substituted by $C_{1-3}$ alkyl or $NR^cR^d$;

$R^c$ and $R^d$ may each independently represent hydrogen, or $C_{1-3}$ alkyl or when part of a group $NR^cR^d$, $R^c$ and $R^d$ together with the nitrogen atom may form a 5 or 6 membered heterocyclic ring optionally containing other heteroatoms, which heterocyclic ring may optionally be substituted further by one or more $C_{1-3}$ alkyl groups;

$R^e$ represents $C_{1-3}$ alkyl and physiologically acceptable solvates and salts thereof, provided that the compound is not 2-chloro-5'-deoxy-5'-fluoro-N-(1-piperidinyl) adenosine or 2-chloro-5'-deoxy-5'-fluoro-N-benzyloxyadenosine.

2. The compound according to claim 1 wherein $R^3$ represents $C_{1-3}$ fluoroalkyl group.

3. The compound according to claim 2 wherein $R^3$ represents $MeCF_2$— or $FCH_2$—.

4. The compound according to claim 1 wherein $R^2$ represents H, methyl or halo.

5. The compound according to claim 4 wherein $R^2$ represents H or chloro.

6. The compound according to claim 1 wherein $R^1$ represents (alk)$_n$—$C_{3-6}$-cycloalkyl wherein n is 0 and 1 and the cycloalkyl is unsubstituted or substituted by at least one substituent which is halogen or OH.

7. The compound according to claim 6 wherein n represents zero.

8. The compound according to claim 6 wherein the cycloalkyl is 5 membered and is monosubstituted with OH or fluorine.

9. The compound according to claim 1 wherein $R^1$ represents a substituted or unsubstituted aliphatic heterocyclic group, the substituent being selected from the group consisting of —$CO_2$—($C_{1-4}$)alkyl, —CO—($C_{1-3}$)alkyl, —$S(=O)_n$—($C_{1-3}$)alkyl, $CONR^aR^b$ (wherein $R^a$ and $R^b$ are defined in claim 1, and when there is a heteroatom S in the ring this heteroatom may optionally be substituted by $(=O)_n$ where n is 1 or 2.

10. The compound according to claim 9 wherein the heterocyclic ring is unsubstituted or substituted with —$CO_2$—($C_{1-4}$)alkyl, or when the heteroatom is S, the substituent $(=O)_n$ is attached to the heterocyclic sulfur atom.

11. The compound according to claim 9 wherein the heteroatom is N and the substituent is $CO_2(C_{1-4})$alkyl is attached to the N atom.

12. The compound according to claim 9 wherein the heterocyclic ring is 6 membered and contains only one heteroatom.

13. The compound according to claim 1 wherein $R^1$ represents a phenyl group substituted by one or more substituents which are OH or halogen.

14. The compound according to claim 13 wherein the phenyl group is disubstituted in the 2,4 positions.

15. The compound according to claim 14 wherein both substituents are halogen.

16. The compound according to claim 15 wherein the 2 substituent is fluoro and the 4 substituent is chloro.

17. The compound according to claim 1 which is:

5'-deoxy-5'-fluoro-N-(tetrahydro-pyran-4-yl)-adenosine,
5'-deoxy-5'-fluoro-2-methyl-N-(tetrahydro-pyran-4-yl)-adenosine,
2-chloro-5'-deoxy-5'-fluoro-N-(tetrahydro-pyran-4-yl)-adenosine,
(2R,3R,4S,5S)-2-[2-chloro-6-(tetrahydro-pyran-4-ylamino)-purin-9-yl]-5 trifluoromethyl-tetrahydro-furan-3,4-diol,
2-chloro-5'-deoxy-5'-fluoro-N-(2R-fluoro-cyclopent-(R)-yl)-adenosine,
2-chloro-5'-deoxy-5'-fluoro-N-(2S-hydroxy-cyclopent-(S)-yl)-adenosine,
N-(endo-bicyclo[2.2.1]hept-2-yl)-2-chloro-5'-deoxy-5'-fluoro-adenosine,
4-[2-chloro-9-(5S-fluoromethyl-3R, 4S-dihydroxy-tetrahydro-furan-2R-yl)-9H-purin-6-ylamino]-piperidine-1 carboxylic acid ethyl ester,
1-{4-[2-chloro-9-(5S fluoromethyl-3R,4S-dihydroxy-tetrahydro-furan-2R-yl)-9H purin-6-ylamino]piperidin-1-yl}-ethanone,
N-(endo-bicyclo[2.2.1]hept-2-yl)-5'deoxy-5'-fluoro-adenosine,
N-(exo-bicyclo[2.2.1]hept-2-yl)-5'-doxy-5'fluoro-adenosine,
5'-deoxy-5'-fluoro-N-(2S-hydroxy-cyclopent-(S)-yl)-adenosine,
4-[9-(5S-fluoromethyl-3R,4S-dihydroxy-tetrahydro-furan-2R-yl)-9H-purin-6-ylamino]-piperidine-1 carboxylic acid ethyl ester,
2-chloro-5'-deoxy-N-(1,1-dioxo-hexahydro-1.delta.6-thiopyran-4-yl)-5'-fluoro-adenosine,
2-chloro-5'-deoxy-N-(2,3-dihydroxy-propyl)-5'-fluoro-adenosine,
(2R,3R,4S,5S)-2-[6-(cyclopropylmethyl-amino)-purin-9-yl]-(1,1-difluoroethyl)-tetrahydro-furan-3,4-diol,
(2R,3R,4S,5S)-2-[6 (bicyclo[2.2.1]hept-2-ylamino)-purin-9-yl]-5-(1,1-difluoroethyl)-tetrahydro-furan-3,4-diol,
2-[9-(5S-fluoromethyl-3R,4R-dihydroxy-tetrahydro-furan-2R-yl)-9H-purin-6-ylamino]-ethanesulfonic acid methylamide, 5'-deoxy-5'-fluoro-N-(2,2-dimethyl-propyl)-adenosine,
N-tert-butyl-5'-deoxy-5'-fluoro-adenosine,
5'-deoxy-5'-fluoro-N-(tetrahydro-thiopyran-4-yl)-adenosine,
2-chloro-5'-deoxy-5'-fluoro-N-isobutyl-adenosine,
2-chloro-5'-deoxy-5'-fluoro-N-(1-methanesulfonylpiperidin-4-yl)-adenosine,
2-chloro-5'-deoxy-N-(2,2-dimethyl-propyl)-5'-fluoro-adenosine,
N-(exo-bicyclo[2.2.1]hept-2-yl)-2-chloro-5'-deoxy-5'-fluoro-adenosine,
4-[2-chloro-9-(5S-fluoromethyl-3R,4S,-dihydroxy-tetrahydro-furan-2R-yl)-9H-6-ylamino]-piperidine-1-carboxylic acid butyl ester,
5'-deoxy-N-(1,1-dioxo-hexahydro-1, delta,6-thiopyran-4-yl)-5'-fluoroadenosine,
N-(4-chloro-2-fluoro-phenyl)-5'-deoxy-5'-fluoroadenosine, or
4-[2-chloro-9-(5S-fluoromethyl-3R,4S-dihydroxy-tetrahydro-furan-2R-yl)-9H-purin-6-ylamino]piperidine-1-carboxylic acid ethylamide.

18. The compound according to claim 1 which exhibits little or no activity at the adenosine $A_3$ receptor.

19. A pharmaceutical composition comprising a compound according to claim 1 together with a pharmaceutical carrier and/or excipient.

20. A method of treating a patient suffering from a condition where there is an advantage in decreasing plasma free fatty acid concentration or reducing heart rate or which patent is suffering from or is susceptible to ischemic heart disease, peripheral vascular disease or stroke or which patient is suffering pain by administration of an effective amount of a compound of claim 1 or a pharmaceutical composition containing a compound of claim 1.

21. A process for the preparation of a compound according to claim 1 which comprises reacting a compound of formula (II):

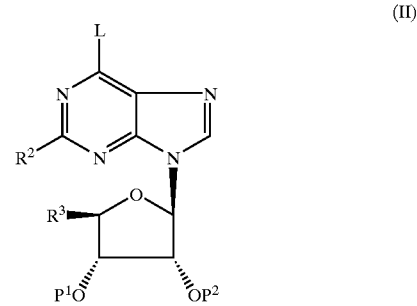

wherein L represents a leaving group, $R^1$, $R^2$ and $R^2$ are as defined in claim 1 and $P^1$ and $P^2$ represent hydrogen or a protecting group, with a compound of formula $R^1NH^2$ or a salt thereof under basic conditions.

* * * * *